(12) United States Patent
Schabbach et al.

(10) Patent No.: US 11,596,744 B2
(45) Date of Patent: *Mar. 7, 2023

(54) SENSOR FOR A DRUG DELIVERY DEVICE

(71) Applicant: SANOFI-AVENTIS DEUTSCHLAND GMBH, Frankfurt am Main (DE)

(72) Inventors: Michael Schabbach, Frankfurt am Main (DE); Christian Nessel, Frankfurt am Main (DE); Daniel Auernhammer, Frankfurt am Main (DE); Beate Franke, Frankfurt am Main (DE); Francisco Soares, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 19 days.

This patent is subject to a terminal disclaimer.

(21) Appl. No.: 17/230,165

(22) Filed: Apr. 14, 2021

(65) Prior Publication Data
US 2021/0236734 A1 Aug. 5, 2021

Related U.S. Application Data

(63) Continuation of application No. 15/748,756, filed as application No. PCT/EP2016/067811 on Jul. 26, 2016, now Pat. No. 11,020,529.

(30) Foreign Application Priority Data

Jul. 31, 2015 (EP) .................................. 15179213

(51) Int. Cl.
*G01F 23/263* (2022.01)
*A61M 5/24* (2006.01)
(Continued)

(52) U.S. Cl.
CPC ............ *A61M 5/24* (2013.01); *A61M 5/1684* (2013.01); *G01F 11/027* (2013.01);
(Continued)

(58) Field of Classification Search
CPC ................. A61M 2205/3389; A61J 2200/76
See application file for complete search history.

(56) References Cited

U.S. PATENT DOCUMENTS

| 4,984,462 A | 1/1991 | Hass, Jr. et al. |
| 6,110,148 A | 8/2000 | Brown et al. |

(Continued)

FOREIGN PATENT DOCUMENTS

| CN | 1545681 | 11/2004 |
| CN | 101405582 | 4/2009 |

(Continued)

OTHER PUBLICATIONS

PCT International Preliminary Report on Patentability in International Application No. PCT/EP2016/067811, dated Feb. 6, 2018, 8 pages.

(Continued)

*Primary Examiner* — Herbert K Roberts
(74) *Attorney, Agent, or Firm* — Fish & Richardson P.C.

(57) ABSTRACT

In one aspect the present disclosure relates to a sensor for measuring at least one physical or chemical parameter of a cartridge filled with a liquid substance. In a further aspect the disclosure relates to a drug delivery device equipped with such a sensor, wherein the sensor includes a planar flexible foil having a first section and having a second section separated from the first section, at least one measurement electrode located on the flexible foil, wherein the flexible foil is wrappable into a wrapped configuration in which the foil forms at least a first wrap with an inner diameter that is equal to or larger than an outer diameter of (Continued)

the cartridge, wherein in the wrapped configuration the first section and the second section at least partially overlap, at least one fastener located in one of the first and second section and configured to attach to the other one of the first and second sections for keeping the flexible foil in the wrapped configuration.

20 Claims, 6 Drawing Sheets

(51) Int. Cl.
    *A61M 5/168*     (2006.01)
    *G01F 11/02*     (2006.01)
    *A61M 5/145*     (2006.01)
    *A61M 5/20*     (2006.01)
    *G01F 1/56*     (2006.01)

(52) U.S. Cl.
    CPC .......... *G01F 23/266* (2013.01); *G01F 23/268* (2013.01); *A61J 2200/76* (2013.01); *A61M 5/1452* (2013.01); *A61M 5/20* (2013.01); *A61M 2205/3317* (2013.01); *A61M 2205/3368* (2013.01); *A61M 2205/3389* (2013.01); *G01F 1/56* (2013.01)

(56) References Cited

U.S. PATENT DOCUMENTS

| | | |
|---|---|---|
| 6,830,558 B2 | 12/2004 | Flaherty et al. |
| 9,186,465 B2 | 11/2015 | Jorgensen et al. |
| 9,486,586 B2 | 11/2016 | Jugl et al. |
| 9,849,252 B2 | 12/2017 | Armes |
| 10,895,487 B2 | 1/2021 | Schabbach et al. |
| 10,898,647 B2 | 1/2021 | Schabbach et al. |
| 11,007,322 B2 | 5/2021 | Schabbach et al. |
| 2001/0037680 A1 | 11/2001 | Buck et al. |
| 2002/0188259 A1 | 12/2002 | Hickle et al. |
| 2003/0034785 A1 | 2/2003 | Palata |
| 2004/0025877 A1 | 2/2004 | Crowder et al. |
| 2005/0154345 A1 | 7/2005 | Milleker et al. |
| 2007/0270744 A1 | 11/2007 | Dacquay et al. |
| 2009/0069756 A1 | 3/2009 | Larsen |
| 2009/0318876 A1 | 12/2009 | Hansen et al. |
| 2010/0102799 A1 | 4/2010 | Schnidrig |
| 2010/0286654 A1 | 11/2010 | Dos Santos et al. |
| 2011/0004188 A1 | 1/2011 | Shekalim |
| 2011/0009824 A1 | 1/2011 | Yodfat et al. |
| 2011/0270188 A1 | 11/2011 | Caffey et al. |
| 2013/0150689 A1 | 6/2013 | Shaw-Klein |
| 2014/0076766 A1* | 3/2014 | Key ............... G09F 3/0292 206/459.5 |
| 2014/0296823 A1 | 10/2014 | Ward et al. |
| 2015/0122015 A1* | 5/2015 | Leppard ......... G01F 23/266 73/304 C |
| 2015/0126963 A1 | 5/2015 | Despa et al. |
| 2015/0268656 A1* | 9/2015 | Bammer ......... G05B 19/188 700/231 |
| 2016/0151558 A1 | 6/2016 | Tobescu |
| 2017/0011970 A1 | 1/2017 | Cheng et al. |
| 2017/0119970 A1 | 5/2017 | Bammer et al. |
| 2017/0119971 A1 | 5/2017 | Marsh et al. |
| 2021/0116287 A1 | 4/2021 | Schabbach et al. |

FOREIGN PATENT DOCUMENTS

| | | | | |
|---|---|---|---|---|
| CN | 101405749 | 4/2009 | | |
| CN | 101484783 | 7/2009 | | |
| CN | 102019011 | 4/2011 | | |
| CN | 104582765 | 4/2015 | | |
| CN | 104740714 | 7/2015 | | |
| CN | 104812424 | 7/2015 | | |
| DE | 3329689 | 3/1984 | | |
| DE | 3329689 A | * 3/1984 | ............... | G01F 1/58 |
| EP | 2182456 | 5/2010 | | |
| EP | 2284849 | 2/2011 | | |
| EP | 2982400 | 2/2016 | | |
| JP | S58-149878 | 9/1983 | | |
| JP | S59-034117 | 4/1985 | | |
| JP | S60-059120 | 4/1985 | | |
| JP | 2005-514965 | 5/2005 | | |
| JP | 2009-522031 | 6/2009 | | |
| JP | 2009-542388 | 12/2009 | | |
| JP | 2012-507314 | 3/2012 | | |
| JP | 2013-506444 | 3/2015 | | |
| JP | 2015-511836 | 4/2015 | | |
| JP | 2015-532136 | 11/2015 | | |
| WO | WO 2006/021295 | 3/2006 | | |
| WO | WO 2007/077224 | 7/2007 | | |
| WO | WO 2007/107558 | 9/2007 | | |
| WO | WO 2007/107562 | 9/2007 | | |
| WO | WO 2008/003625 | 1/2008 | | |
| WO | WO 2010/052275 | 5/2010 | | |
| WO | WO 2011/039205 | 4/2011 | | |
| WO | WO 2013/050535 | 4/2013 | | |
| WO | WO 2013/120775 | 8/2013 | | |
| WO | WO 2014/052997 | 4/2014 | | |
| WO | WO 2014/118111 | 8/2014 | | |
| WO | WO 2014/139914 | 9/2014 | | |

OTHER PUBLICATIONS

PCT International Preliminary Report on Patentability in International Application No. PCT/EP2016/067813, dated Feb. 6, 2018, 8 pages.
PCT International Preliminary Report on Patentability in International Application No. PCT/EP2016/067814, dated Feb. 6, 2018, 8 pages.
PCT International Preliminary Report on Patentability in International Application No. PCT/EP2016/067815, dated Feb. 6, 2018, 10 pages.
PCT International Search Report and Written Opinion in International Application No. PCT/EP2016/067811, dated Nov. 3, 2016, 11 pages.
PCT International Search Report and Written Opinion in International Application No. PCT/EP2016/067813, dated Nov. 3, 2016, 11 pages.
PT International Search Report and Written Opinion in International Application No. PCT/EP2016/067814, dated Nov. 2, 2016, 11 pages.
PCT International Search Report and Written Opinion in International Application No. PCT/EP2016/067815, dated Nov. 3, 2016, 12 pages.
English translation of DE3329689. (Year: 1984).
U.S. Appl. No. 15/748,898, filed Jan. 30, 2018, Michael Schabbach.
U.S. Appl. No. 15/748,217, filed Jan. 29, 2018, Michael Schabbach.
U.S. Appl. No. 15/748,309, filed Jan. 29, 2018, Michael Schabbach.
U.S. Appl. No. 17/116,477, filed Jan. 9, 2020, Michael Schabbach.

* cited by examiner

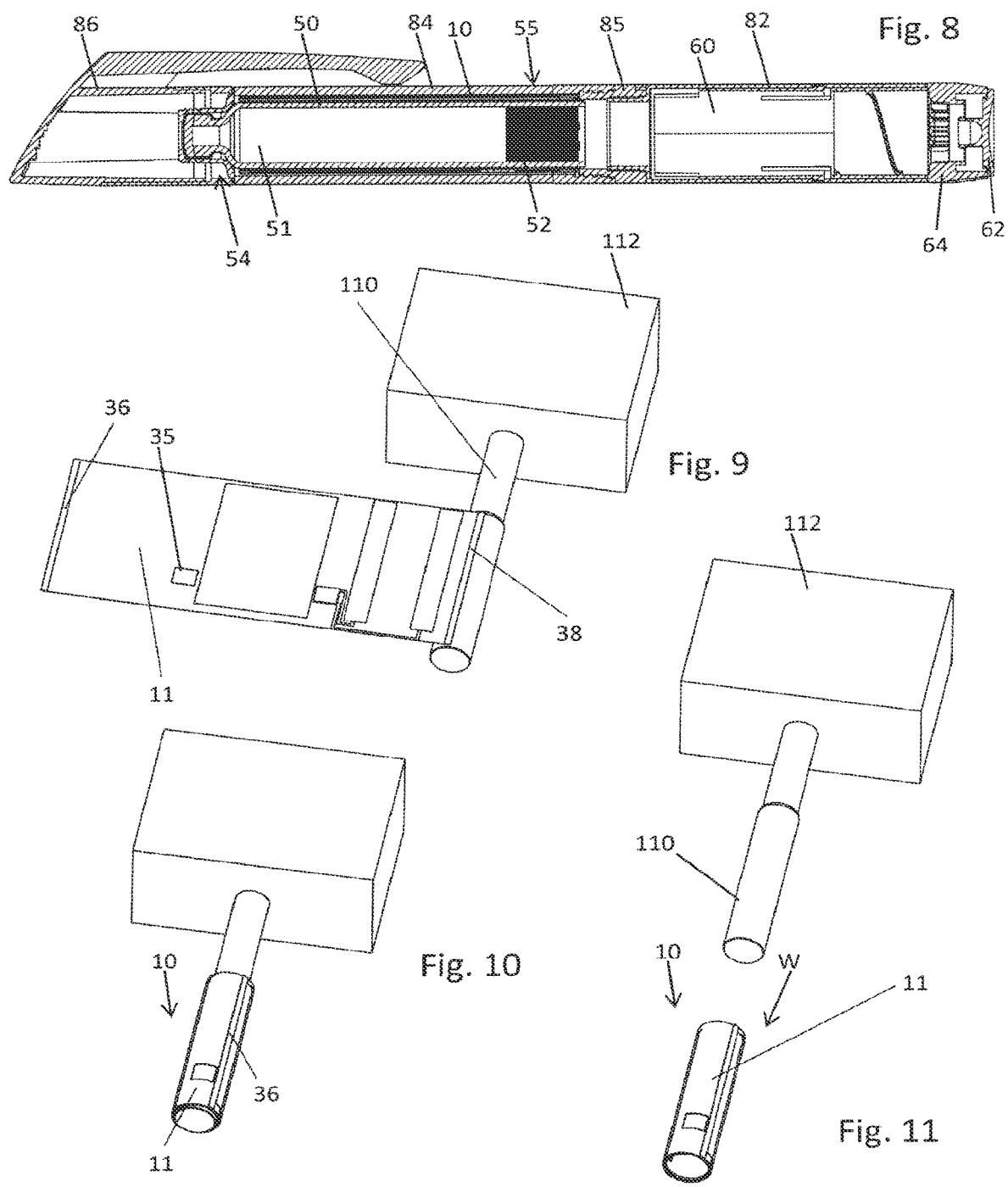

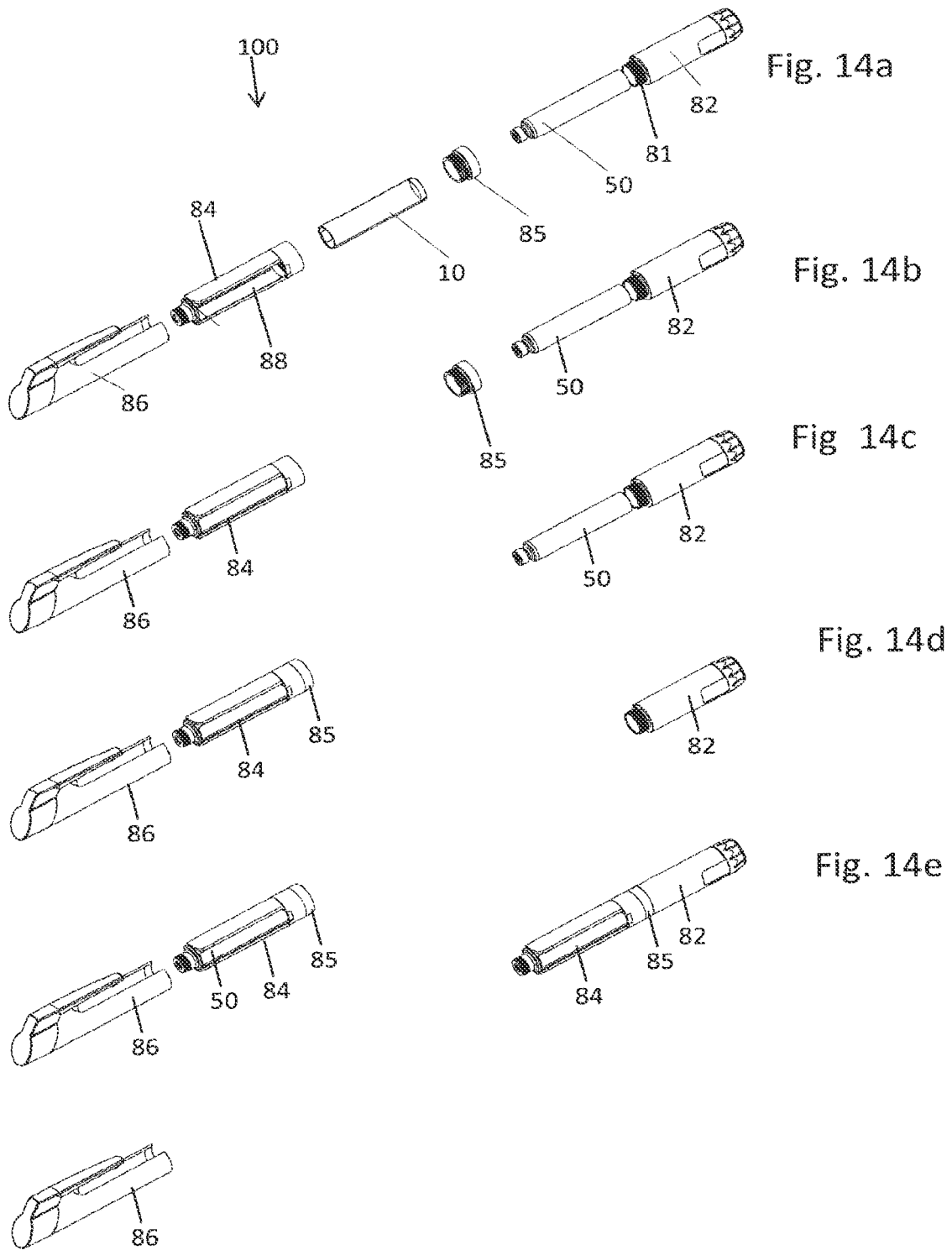

SENSOR FOR A DRUG DELIVERY DEVICE

CROSS REFERENCE TO RELATED APPLICATIONS

The present application is a continuation application of U.S. patent application Ser. No. 15/748,756, filed on Jan. 30, 2018, which is the national stage entry of International Patent Application No. PCT/EP2016/067811, filed on Jul. 26, 2016, and claims priority to Application No. EP 15179213.2, filed on Jul. 31, 2015, the disclosures of which are expressly incorporated herein in entirety by reference thereto.

TECHNICAL FIELD

The present disclosure relates to the field of measuring at least one physical or chemical parameter of a cartridge filled with a liquid substance, typically filled with a medicament. In another aspect the disclosure relates to a drug delivery device, in particular to an injection device for setting and dispensing of a dose of a liquid medicament.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices such as pen-type injectors have to meet a number of user-specific requirements. For instance, with patient's suffering chronic diseases, such as diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been dispensed or used-up.

It is generally desirable to determine the amount of medicament remaining in a cartridge while the cartridge is arranged inside a drug delivery device. It is generally known in the prior art to implement a capacitive measurement or capacitive determination of a filling level of a cartridge. For this either on the cartridge itself or at the interior of a cartridge holder section of the drug delivery device there are provided at least two electrodes. Since the dielectric properties of the liquid substance inside the cartridge clearly differ from those of other surrounding materials, such like the vitreous material the cartridge is made of the rubber-based material forming the proximal piston of the cartridge, the electrical capacity to be measured between the electrodes located on radially oppositely located sidewall portions of the cartridge correlates with the filling level of the cartridge and/or with the axial position of the piston inside the cartridge.

For instance, document WO 2014/052997 A1 discloses a respective dispensing device having at least one pair of capacitive measurement electrodes that are arranged in the outer region of a medicament container for determining the permittivity of the respective medium in an intermediate region between the measurement electrodes. Furthermore, there is described a shield that is arranged around the container and which surrounds the measurement materials in a sheath-like manner.

In order to conduct a precise measurement of a physical or chemical parameter of the cartridge and in particular for measuring the filling level of the liquid substance contained therein it is necessary to arrange at least one or several measurement electrodes to the outer circumference of the barrel of the cartridge. The correct position of the electrodes relative to the cartridge may be of particular relevance to obtain precise and reliable measurement results. It is generally conceivable to fixedly attach electrodes as well as electronic components of a sensor to the outer circumference of a cartridge but this would remarkably increase the total costs for manufacturing of the cartridge. Document WO 2014/052997 further suggests use of a particular carrier for carrying measurement electrodes. There, the carrier may be part of the drug delivery device. Providing of such an additional carrier requires a substantial redesign of existing drug delivery devices which is to be avoided.

In some aspects, the present disclosure provides a sensor for measuring at least one physical or chemical parameter of a cartridge filled with a liquid substance. The sensor should provide reliable and precise measurement of a desired parameter, in particular of a filling level of the cartridge. Moreover, the sensor should be suitable for implementation into existing drug delivery devices or into existing concepts of drug delivery devices so that use of the sensor inside or with the drug delivery device only requires a minimum of modifications to be made to the drug delivery device. In addition, the sensor should be operable with standardized and commercially distributed cartridges as they are widely known in the art. Consequently, the operation of the sensor for measuring the at least one physical or chemical parameter should avoid and circumvent the necessity of making any modifications to the cartridge.

SUMMARY

In one aspect the disclosure relates to a sensor for measuring at least one physical or chemical parameter of a cartridge, wherein the cartridge is filled with a liquid substance. Typically, the cartridge is filled with a liquid medicament. The cartridge may comprise a tubular-shaped barrel, e.g. made of glass or some other material substantially inert to the liquid substance contained therein.

The sensor comprises a planar flexible foil having a first section and having a second section separated from the first section. In other words, first and second sections of the planar flexible foil are non-overlapping. They are completely separated from each other. Furthermore, they are arranged at a predefined distance with respect to each other. The sensor further comprises at least one measurement electrode located on the flexible foil. The flexible foil is further wrappable or coilable into a wrapped or coiled configuration, in which the foil forms at least a first wrap with an inner diameter that is equal to or larger than an outer diameter of the cartridge.

Typically, the flexible foil is wrappable into a tubular structure or tubular sheath so as to receive the tubular-shaped cartridge therein. The at least first wrap is typically folded or wrapped in such a way that the cartridge is insertable into said first wrap along a longitudinal direction, wherein said longitudinal direction coincides with the axial direction or longitudinal axis of the tubular-shaped first wrap.

The sensor further comprises at least one fastener located in the first section of the flexible foil. The fastener is configured to attach to the second section of the foil for keeping the flexible foil in the wrapped configuration. By means of the fastener to attach to the second section the first and second sections of the flexible foil are kept together so as to prevent an automatic unwrapping or de-coiling of the flexible foil. By means of the fastener, a stable and self-supporting tubular sheath can be formed simply by wrapping the planar flexible foil and by attaching the at least one fastener to the second section thereof.

By means of the at least one fastener initially planar flexible foils and initially planar sensors can be wrapped to form a tubular-shaped sheath. Once such a sheath is formed the wrapped sensor or the wrapped planar flexible foil with the at least one measurement electrode located thereon can be easily assembled and positioned inside a housing of the drug delivery device. Inserting of a wrapped flexible foil into a correspondingly-shaped tubular receptacle of the housing of the drug delivery device is rather straight forward. For this, the drug delivery device, in particular its housing only has to provide a correspondingly-shaped receptacle, in which the wrapped flexible foil, i.e. the wrapped sensor can be positioned and fixed.

The at least one fastener therefore facilitates the process of assembly and helps to keep the sensor in a predefined geometric shape even before it is assembled inside the drug delivery device. The predefined geometric shape is just defined by the position of the fastener and the correspondingly-configured first or second sections of the foil. If for instance a receptacle of a drug delivery device to receive a wrapped or coiled flexible foil is subject to inevitable manufacturing tolerances, the diameter of the wrapped foil will be presumably subject to at least slight modifications as the flexible foil tends to unwrap once it is located inside the receptacle. Only a slight but uncontrolled unwrapping or unfolding of an initially folded or wrapped flexible sensor could have detrimental effects on the precision and reproducibility signals measured by the sensor. With the fastener a series of identically wrapped sensors can be provided with a high degree of reproducibility and accuracy. This allows improving the reproducibility as well as the precision of data or signals to be measured with the respective sensor.

In addition, the at least one fastener serves to keep the flexible foil in the wrapped configuration. In the wrapped or coiled configuration the planar flexible foil inherently exhibits an increased mechanical stability so that it is no longer required to provide a separate carrier in the drug delivery device to act as a mechanical support structure for the sensor. In this way modifications to be made to the drug delivery device for receiving and for accommodating a wrapped flexible foil can be kept to a minimum.

When the flexible foil is wrapped or coiled into the wrapped configuration the first section and the second section thereof at least partially overlap. Consequently, first and second sections of the planar flexible foil are selected and defined in such a way that they overlap in radial direction. Here, the radial direction refers to the geometry of the tubular-shaped cartridge or the tubular-shaped wrapped flexible foil. The radial direction extends substantially perpendicular to the plan of the initially planar foil. So the first and second sections are located at well-defined portions of the planar flexible foil, which portions get in direct overlapping contact as the planar flexible foil is transferred into its wrapped configuration. The planar flexible foil typically has a rectangular structure with four side edges.

The planar flexible foil is coilable or wrappable with regard to an imaginary coil axis or wrap axis that extends parallel to a lateral side edge of the foil. The initially planar flexible foil extends in a longitudinal direction and a lateral direction. Upon a final assembly, e.g. in a drug delivery device also housing the cartridge the longitudinal direction of the wrapped flexible foil extends substantially parallel or co-aligns with the longitudinal or axial direction of the tubular-shaped cartridge. The lateral direction of the planar flexible foil extends along the outer circumference of the tubular-shaped sidewall of the cartridge. In other words when wrapped in the wrapped configuration the lateral direction of the flexible foil extends in tangential direction around the tubular-shaped sidewall of the barrel of the cartridge.

According to an embodiment the fastener is positioned at a lateral side edge of the flexible foil. In this way, a lateral end, hence an end of a coiled or wrapped configuration of the flexible foil can be attached to a wrap located underneath. Providing the fastener at a lateral side edge a rather closed and compact structure of the wrapped sensor can be provided. Making use of a fastener at a lateral side edge of the flexible foil, which side edge being the last edge of the flexible foil to be bended or coiled onto a winding or wrap located underneath the wrapped configuration of the flexible foil and hence the wrapped configuration of the sensor is somewhat tubular-shaped without any substantial radial protrusions at its outside-facing sidewall or at its inside-facing sidewall.

With a rather low thickness of the flexible foil and the number of wraps or windings to be formed until the initially planar flexible foil is completely coiled up, the finally obtained wrapped configuration, e.g. in form of a tubular-shaped coil of the planar flexible foil may comprise a rather thin sidewall that enables a smooth and easy integration and assembly of the sensor inside the drug delivery device.

According to another embodiment the fastener located in the first section comprises an adhesive and is hence adhesively attachable to the second section of the flexible foil when the flexible foil is in the wrapped configuration. In particular and when the fastener is located at a lateral side edge of the flexible foil that is coiled up last, when the flexible foil is transferred into its wrapped configuration, it is of particular benefit when the fastener extends in longitudinal or axial direction all along said lateral side edge and that the fastener is completely provided with an adhesive. In this way, the entire lateral side edge of the flexible foil can be attached to the second section, hence to a wrap, coil or winding of the foil located radially underneath. In this way a rather smooth-shaped outer surface of the wrapped sensor can be provided, which is of particular benefit for a smooth assembly and insertion of the coiled sensor into a respective receptacle or compartment of the housing of the drug delivery device along a longitudinal direction.

According to another embodiment the fastener located in the first section comprises a bondable or weldable structure for bonding or welding to the second section of the flexible foil when the flexible foil is in the wrapped configuration. Here, the fastener may comprise a particular chemically or thermally sensitive material or a respective strip of material that may extend all along the lateral side edge of the flexible foil. Bonding or welding may be induced by means of chemical agents and/or by application of thermal energy once the flexible foil is in its wrapped configuration. It is generally conceivable, that any arbitrary section of the planar flexible foil is bonded or welded to an overlapping and adjacently-located section of the flexible foil as the wrapped configuration is formed.

In this way and according to this particular embodiment the at least one fastener may be located anywhere across the planar flexible foil. It is generally conceivable, that the at least one fastener consists of a predefined section, typically of the second section as already mentioned above. When the second section substantially overlaps with the fastener in a wrapped or coiled up configuration the fastener and optionally also the second typically located radially underneath may become subject to a welding procedure thereby forming a permanent and non-releasable coil or wrapped configuration of the sensor and its flexible foil.

According to a further embodiment the fastener and the second section are located on opposite sides of the flexible foil. In an initial planar configuration of the flexible foil the fastener may be provided on an upper side of the foil whereas the second section to be attached or connected with the fastener is located on an opposite side of the flexible foil, hence at a lower side thereof. When in the wrapped configuration, the fastener may be provided on an inside-facing side of the wrapped foil whereas the second section may be provided on an outside-facing side of the wrapped foil. In this way and when formed to a tubular-shaped coil the fastener located in the first section is in direct contact with the second section. In other configurations or embodiments it is also conceivable, that the fastener and the second section are located in the flexible foil or extend through the flexible foil. With such embodiments the fastener and the second section are configured to form a positive interlock to inhibit an automatic unfolding or de-coiling of the wrapped or coiled flexible foil.

According to a further embodiment the fastener is located in the first section and protrudes from the plane of the flexible foil. Correspondingly, the second section comprises a recess to receive the fastener when the flexible foil is in the wrapped configuration. In this way a positive interlock of the protruding fastener and the recessed portion of the flexible foil can be obtained. Typically, the recess and the fastener are separated at a distance in lateral direction that corresponds to the circumference of the at least first wrap. Moreover, with regards to the longitudinal or axial direction the fastener and the recess substantially overlap. So when wrapped around an imaginary tubular-shaped barrel of the cartridge the protruding fastener fits into the recess as the at least first wrap is formed. Due to this type of positive interlock the wrapped or coiled flexible foil is hindered to unwrap or to de-coil automatically. By means of the at least one fastener engaged with the recess a rather stable and self-supporting configuration of a coiled sensor is obtained that is particularly suitable for insertion into a correspondingly-shaped receptacle of a housing of a drug delivery device in a longitudinal direction.

Irrespective of the specific attachment of fastener and second section of the flexible foil the mutual fastening prevents a mutual longitudinal or axial displacement of e.g. the first wrap and further wraps, e.g. a second or third wrap as the wrapped sensor is for instance inserted into a receptacle of a drug delivery device in longitudinal direction. So the interlock obtainable by the fastener attached to the second section does not only act in lateral but also in longitudinal direction.

In another embodiment the sensor further comprises a processor electrically connected to the at least one measurement electrode, wherein the at least one measurement electrode is located in a sensing zone of the flexible foil. Typically, the processor comprises at least two measurement electrodes, that are both electrically connected to the processor. The processor, typically implemented as a microcontroller or similar data processing device, is attached to the flexible foil. It is typically arranged in the sensing zone or beneath the sensing zone, typically in a lateral border region of the sensing zone of the flexible foil.

In addition and according to a further embodiment the sensor also comprises an antenna located in a communication zone of the flexible foil. The antenna is electrically connected to the processor. The antenna may provide a two-fold function. The antenna may provide wireless communication of the sensor with for instance a reader or a further data processing device, such like a smartphone, tablet computer, personal computer or the like. In addition the antenna may be implemented as a radio-frequency identification (RFID) device. It may be implemented as a near-field communication (NFC) device so that the antenna provides wireless coupling with a source of energy in order to provide electrical energy to the processor and/or to the electrodes. By implementing the antenna as an RFID or NFC component the sensor may act like a passive RFID or NFC device that does not require a separate energy source. In this way the sensor can be void of an own energy source. This enables a low cost and space-saving implementation of such a sensor. Moreover, due to a lack of an own energy source, the overall lifetime of the sensor can be prolonged and does no longer depend of the lifetime of the energy source.

First and second electrodes are not only located in the sensing zone but are permanently and fixedly attached to the flexible foil in the region of its sensing zone. In the same way also the antenna is fixedly attached to the foil in the communication zone that is separated from the sensing zone. By having both, the electrodes as well as the antenna attached to one and the same flexible foil, the flexible foil serves as a common support or base of the sensor. Typically, the at least first and second electrodes as well as the antenna are printed or coated on a surface of the flexible foil, which foil is typically electrically insulating. Hence, the foil actually acts as a flexible planar substrate or mechanical support for both the first and second electrodes and the antenna. Implementation of both, the electrodes and the antenna on one and the same flexible foil is beneficial for an assembly process of sensor and cartridge.

When arranging or attaching the sensing zone of the planar flexible foil to the cartridge the antenna is automatically correctly positioned relative to the cartridge. A separate step of antenna assembly and in particular establishing of a mutual electrical interconnection of first and/or second electrodes with the processor and/or with the antenna may then become superfluous. Moreover, having both, namely first and second electrodes printed on or attached to the planar flexible foil the at least two electrodes are inherently correctly positioned relative to each other. During the assembly of the flexible foil and the cartridge the relative position and/or orientation of the first and second electrodes persists and may only change due to a geometric deformation of the flexible foil.

According to another embodiment the sensor further comprises an electrical shield also located on the flexible foil and being electrically connected to the processor. Typically, the electrical shield extends over the entire communication zone. The electrical shield substantially overlaps with the antenna or completely covers and surrounds the antenna. Typically and in a final assembly configuration the electrical shield is wrapped around the sensing zone so as to serve as a cladding for the sensing zone.

In this way the sensing zone and hence the rather sensitive electrodes thereof can be effectively protected and shielded against any potential variations of the electromagnetic field in the vicinity of the sensor. Moreover, the electrical shield may serve and act as a kind of approach sensor or touch sensor by way of which approaching of e.g. an object, such like a finger in the direct vicinity of the sensor can be detected. In this way the electrical shield not only serves to protect first and second electrodes against EMI emissions but also provides an effective means to compensate or to counteract any detrimental effects of the arrangement of first and second electrodes in response to an approaching of an object that may modify the dielectric properties in the sensor's vicinity.

According to another embodiment the electrical shield is also at least partially located or overlaps with the communication zone. The electrical shield is however electrically isolated from the antenna. The electrical shield and the antenna are further located on opposite sides of the flexible foil. Since the flexible foil is electrically insulating a simple arrangement of antenna and electrical shield on opposite sides, e.g. on an upper side and on a lower side of the flexible foil inherently provides a sufficient electrical insulation therebetween. Moreover, in a final assembly configuration, in which the communication zone is wrapped and receives the outer circumference of the tubular-shaped cartridge, the antenna, typically located on an outside facing portion of the foil, is radially separated from the electrical shield, which is typically located on inside facing portion of the wrapped or coiled flexible foil. In a final assembly configuration in which the flexible foil is wrapped around the tubular barrel of the cartridge the electrical shield is typically radially sandwiched between the communication zone and the sensing zone.

According to another embodiment the foil is substantially transparent. The foil typically comprises or is made of a transparent polymer. The foil may comprise at least one or a combination of the materials polycarbonate, polyimid, or polyvinyl chloride (PVC). Moreover, the foil is printable or coatable with electrically conductive structures, such like with at least first and second electrodes, the antenna or the electrical shield. Moreover, first and second electrodes, processor, antenna as well as electrical shield may be electrically connected by means of several conducting paths that may be simultaneously printed or coated onto the foil. The conducting paths may be of the same material as the antenna, the shield and/or the electrodes. Typically, at least one of the antenna, the shield, the first or second electrodes and the conducting path comprise a metallic and conducting material or even consist of such an electrically conductive material.

The conductive structures on the flexible foil may also be applied by way of coating by any suitable thin film-depositing technology, such like sputtering, spray coating or by means of various chemical vapor-depositing techniques.

By having arranged all electrical components of the sensor on one and the same planar flexible foil, mechanical interfaces, such like plugs or other connectors between the sensor's electrical components become superfluous. Due to the transparent foil and/or the transparent electrodes, conducting path, shield or antenna, the interior of e.g. the vitreous cartridge is still visually inspectable. The electronic components of the sensor, i.e. first and second electrodes, the antenna or the shield may comprise or may consist of indium-tin oxide (ITO) that is conductive and substantially transparent. Alternatively, the electronic components may comprise or consist of a comparable electrically conductive and transparent material.

Due to the transparent foil and/or the transparent electronic structures attached thereto or embedded therein the content of the transparent and vitreous cartridge remains visually inspectable. Visual inspectability of the interior of the cartridge is of particular importance in order to provide an intuitive control whether the content of the cartridge, in particular the liquid medicament might be subject to coagulation or flocculation or some other detrimental effects or phenomena.

In a further embodiment the sensing zone and the communication zone of the flexible foil are adjacently arranged in a lateral direction such that the sensing zone forms the first wrap and the communication zone forms a second wrap enclosing the first wrap when the flexible foil is in the wrapped or coiled configuration. When the at least one measurement electrode and the electrical shield are located on the same side of the flexible foil and when the antenna is located in an overlapping configuration with the electrical shield but on an opposite side of the foil, then the electrical shield is radially sandwiched between the antenna and the measurement electrodes when the sensor is in the wrapped configuration with the measurement electrodes facing radially inwardly and being located in the region of the first or inner wrap or coil.

In another embodiment the flexible foil further comprises a protection zone adjacently located to the communication zone and being configured to form a third wrap enclosing the second wrap when the flexible foil is in the wrapped configuration. In this way the planar flexible foil comprises at least three zones that are adjacently located in the lateral direction. Typically, each one of the at least three zones extends all over the longitudinal extension of the flexible foil, hence from a distal side edge towards a proximal side edge. Starting from a lateral side edge there is first located the sensing zone with the at least one measurement electrode. Opposite to this lateral side edge the communication zone is arranged next to or adjacent to the sensing zone and further in lateral direction there follows the protection zone. In this way the communication zone is laterally sandwiched between the sensing zone and the protection zone.

When in the coiled or wrapped configuration the protection zone just provides a mechanical protection of the first and second wraps located underneath. Since the antenna is typically located on an outside-facing side of the second wrap the protection zone is configured to provide mechanical protection for the antenna. Since the wrapped sensor is configured and intended to be positioned and to be inserted into a receptacle of a drug delivery device in longitudinal or axial direction the protection zone protects the antenna against mechanical influences, such like scratches.

When the fastener is configured as an adhesive stripe or as a bondable or weldable structure it is typically located at a free lateral edge of the protection zone forming a lateral free end of the wrapped flexible foil. In this case the second section may substantially overlap with a transition region between the second wrap and the third wrap while being located on an opposite side of the flexible foil compared to that side on which the at least one adhesive, bondable or weldable fastener is located.

It is generally conceivable that the sensing zone forming the first wrap, the communication zone forming the second wrap and the protection zone forming the third wrap are all of substantially equal lateral dimensions. However, depending on specific demands of the drug delivery device and/or of the cartridge it is also conceivable that the lateral and/or longitudinal extension of sensing zone, communication zone and protection zone vary to a low or large extent.

According to a further aspect the disclosure also relates to a drug delivery device for setting and for dispensing of a dose of a liquid medicament, typically contained in a cartridge. The drug delivery device comprises a housing having a tubular-shaped receptacle to receive and to accommodate a cartridge filled with the medicament. The drug delivery device further comprises a sensor as described above, which sensor is arranged and fixed inside this particular receptacle when the sensor is in its wrapped configuration. In this way the wrapped sensor is configured to receive the cartridge inside the first wrap. When arranged inside the drug delivery device's receptacle the coiled or wrapped sensor forms a kind of a cladding of the inner sidewall of the tubular-shaped receptacle. In a final assembly configuration, in which the cartridge is located inside said receptacle the coiled sensor is radially sandwiched between the cartridge and the sidewall of the receptacle.

The coiled or wrapped configuration of the sensor allows to arrange the sensor inside the receptacle irrespective on the presence of a cartridge. As a cartridge is inserted in the device's receptacle and hence inside the inner wrap of the sensor at least one physical or chemical parameter of the cartridge and/or of its liquid medicament can be actually measured. Since the sensor in its entirety is assembled inside the housing of the drug delivery device the cartridge does not require any modification in order to conduct the intended measurement. The sensor as described herein is configured to operate with conventional cartridges as they are commonly used for the injection of a medicament, typically by making use of a pen-type injection device.

Arrangement of the sensor inside the drug delivery device is of particular advantage for reusable drug delivery devices, wherein the cartridge is intended to be replaced when empty. In this way all components of the sensors including the electronic components as well as the at least one measurement electrode are usable multiple times, i.e. with a series of cartridges. For a measurement to be conducted there are no further modifications to be made to the drug delivery device. When the sensor is implemented as a kind of a passive RFID label or RFID tag a measurement can be triggered and the measurement result can be further processed by a single electronic device, such like a RFID or NFC-capable smartphone or tablet computer.

The sensor does not necessarily have to be implemented as a passive RFID or NFC device. Since the sensor in its entirety is intended to be permanently arranged inside the housing of the drug delivery device it is also conceivable to provide an extra power source for the sensor so that regular or frequent measurements can be conducted in accordance with a predefined measurement schedule irrespective and independent from the presence of a RFID or NFC electronic device. Especially with electronically implemented drug delivery devices an active sensor design rather than a passive NFC or passive RFID power management for the sensor can be implemented. Then, for the operation of the sensor an existing electrical energy supply of the drug delivery device can be used and no extra electrical power source, such like a separate battery would be required.

In a further embodiment the receptacle of the drug delivery device to receive and to accommodation the sensor as well as the cartridge is located in a cartridge holder of the housing. Here, a proximal end section of the cartridge holder actually accommodates the cartridge. In this embodiment the cartridge is actually arranged inside the drug delivery device and forms a replaceable component thereof. The cartridge holder is further detachably connectable with a distal end section of a body of the housing. Typically, the cartridge holder forms a distal portion of the housing whereas the body forms a proximal portion of the housing.

The body further accommodates a drive mechanism, typically comprising a piston rod. The drive mechanism and its piston rod is typically configured to exert distally-directed pressure on a piston of the cartridge, which piston seals the proximal end of the cartridge. The drive mechanism of the drug delivery device is particularly configured to advance in distal direction so as to exert a pressure onto the piston of the cartridge for driving the same in distal direction, thereby expelling a predefined amount, hence a dose of the medicament from a distal outlet of the cartridge. The distal outlet of the cartridge is typically in fluid connection with a needle assembly, such like a double-tipped injection needle for depositing the medicament in biological tissue of a patient.

In a further embodiment the drug delivery device, in particular the cartridge holder comprises a fixing element or a fixing structure to fix the wrapped sensor inside its receptacle. It is for instance conceivable that the proximal end of the cartridge holder comprises numerous latching elements or clip features by way of which the wrapped sensor can be positionally fixed inside the receptacle of the cartridge holder. Furthermore, it is conceivable that the fixing element or the fixing structure of the cartridge holder comprises a removable closure, such like a threaded annular ring or a flange-like element having an outer diameter that matches with the outer diameter of the wrapped sensor and having an inner diameter that is large enough to receive the tubular-shaped barrel of the cartridge therethrough. In this way the sensor can be fixed inside the receptacle with regard to the longitudinal or axial direction while the cartridge is removably arrangeable inside said receptacle.

In the present context the distal direction denotes a dispensing end of the drug delivery device. When the drug delivery device is implemented as an injection device the distal end of the drug delivery device faces towards an injection site of a patient. The proximal end or the proximal direction faces in the opposite longitudinal direction of the device. When implemented as an injection device, such like a pen-type injector, the proximal end of the drug delivery device is operable by a hand of a user so as to configure, to set and to conduct an injection procedure.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-ithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(2)25, Asp28] Exendin-4(1-39)-(Lys)6-NH2,
H-(Lys)6-des Pro36, Pro37, Pro38 [Trp(2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two p sheets create a "sandwich" shape, held together by interactions between conserved cysteines and other charged amino acids.

There are five types of mammalian Ig heavy chain denoted by $\alpha$, $\delta$, $\in$, $\gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antibody contains two light chains that are always identical; only one type of light chain, $\kappa$ or $\lambda$, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as it is defined by the claims. Further, it is to be noted, that any reference numerals used in the appended claims are not to be construed as limiting the scope of the invention.

BRIEF DESCRIPTION OF THE FIGURES

In the following, an embodiment of the display arrangement, the drive mechanism and the drug delivery device is described in detail by making reference to the drawings, in which:

FIG. 8 shows a longitudinal cross-section through the entire drug delivery device in a final assembly configuration, FIG. 9 shows a first stage of wrapping or coiling the sensor, FIG. 10 shows a further stage of coiling the sensor and FIG. 11 shows a final stage of the coiling and fastening process, FIG. 14a-e shows a sequence of assembly of the drug delivery device.

DETAILED DESCRIPTION

Figure 1:
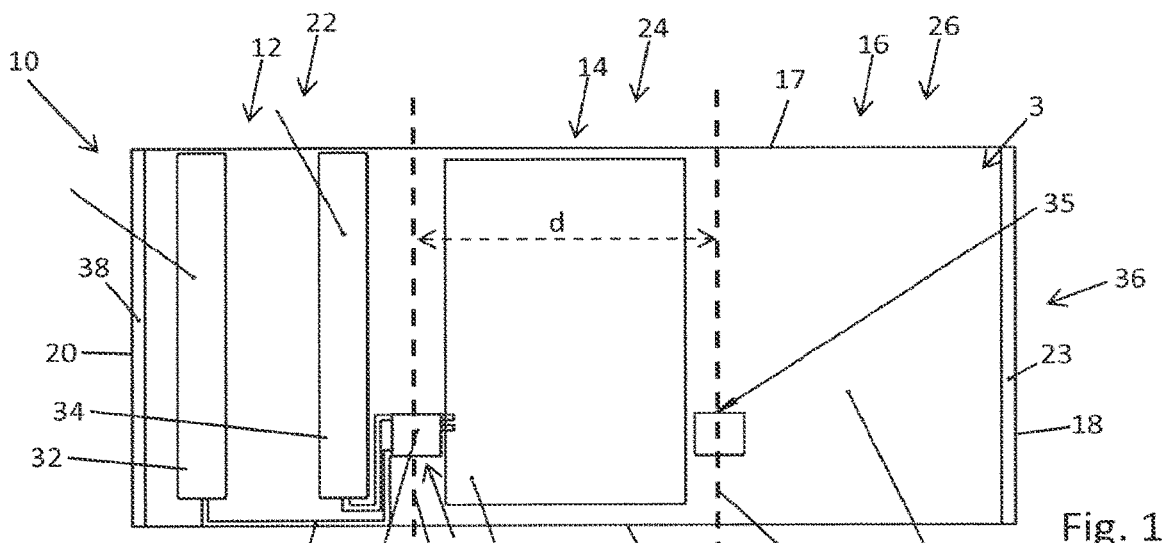
FIG. 1 shows a top view of the sensor in an initially planar or unwrapped configuration.
Figure 2:
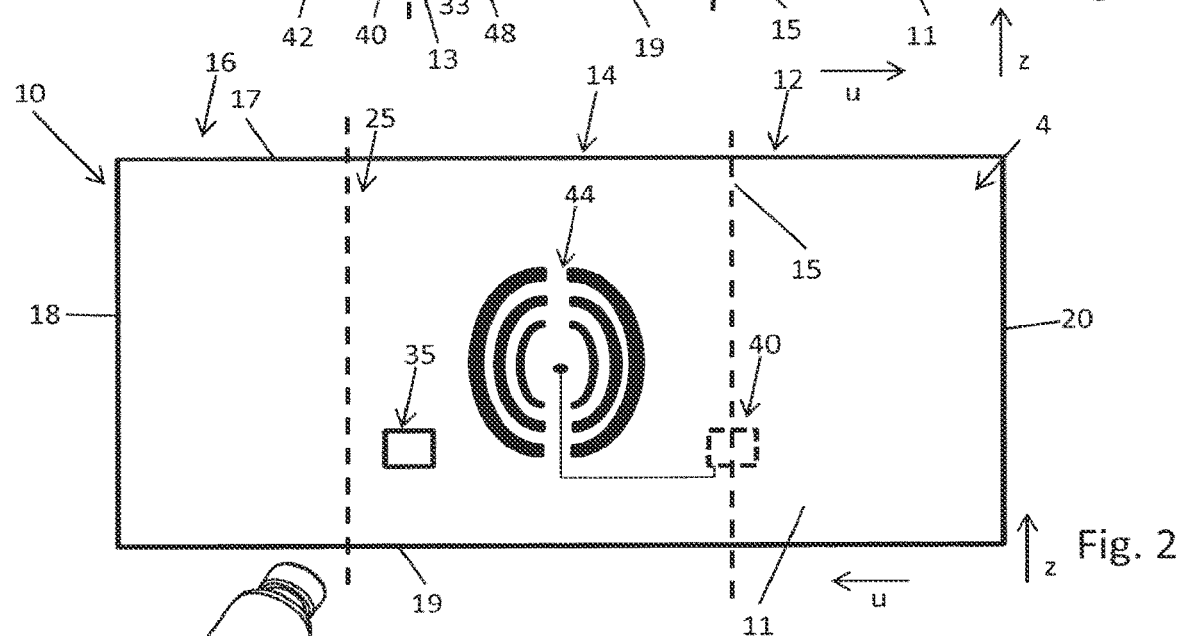
FIG. 2 shows the opposite side of the sensor according to FIG. 1.
Figure 3:
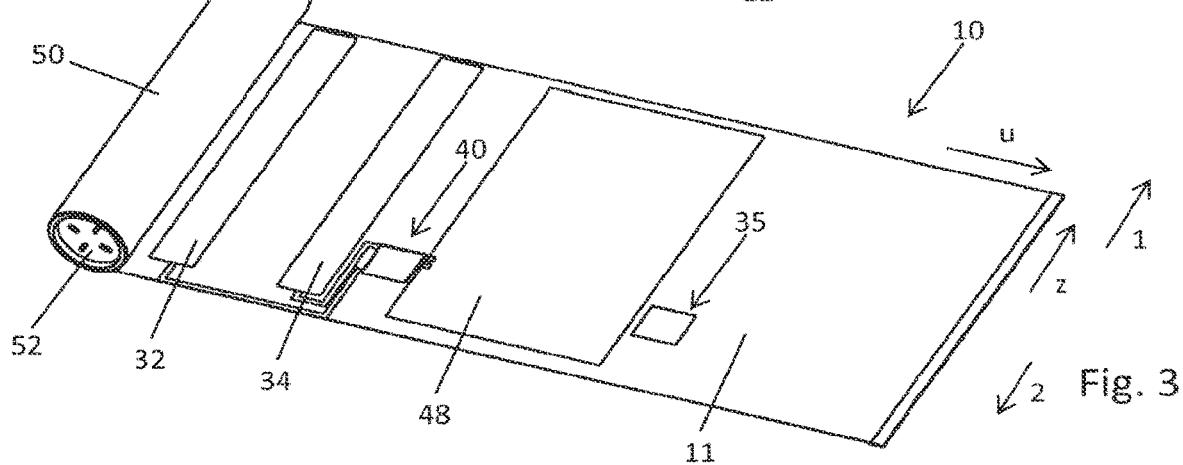
FIG. 3 shows a perspective view of the sensor with regard to the orientation and dimensions of a cartridge filled with the liquid substance.

In FIGS. 1-3 the sensor 10 is illustrated in different views. The sensor 10 comprises a planar flexible foil 11. The flexible foil 11 is of substantially rectangular shape. It comprises four side edges 17, 18, 19, 20. The orientation of the wrapped sensor 10 is given with regard to the orientation of a cartridge 50 containing a liquid substance, typically a medicament 51. The cartridge in a final assembly configuration inside a drug delivery device 100 as shown in FIG. 8 is oriented along a longitudinal direction. An outlet end 54 of the cartridge 50 is pointing in a distal direction 1, whereas a proximal end 55 is located oppositely. As it is apparent from FIGS. 3 and 8, the proximal end of the cartridge 50 is sealed by a piston 52 that is displaceable in longitudinal direction by means of a plunger or piston rod of a drive mechanism 60 of the drug delivery device 100.

Figure 7:
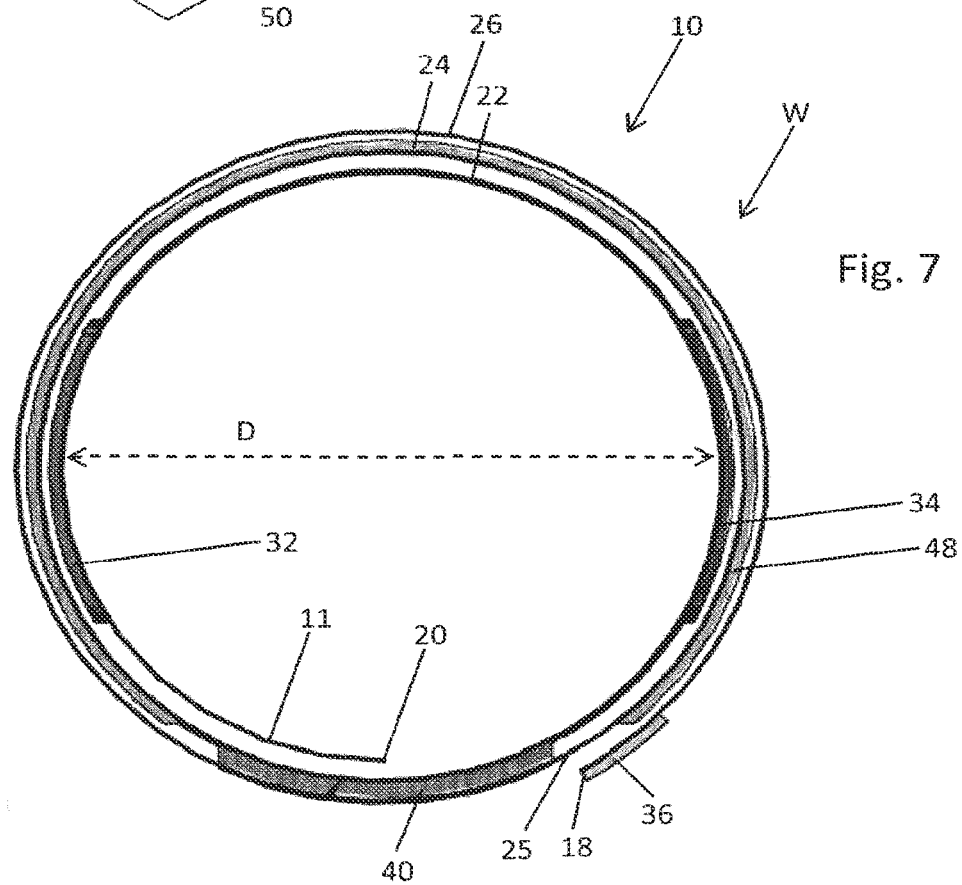
FIG. 7 shows a cross-section through the wrapped sensor.

The sensor 10 is intended to be transferred into a wrapped configuration W as shown in cross-section in FIG. 7. When in the wrapped configuration the tubular-shaped coiled sensor 10 is intended to be oriented parallel to the cartridge 50 inside the drug delivery device 100. Consequently, the oppositely-located side edges 18, 20, also denoted as lateral side edges, extend in longitudinal direction (z) whereas the other two side edges 17, 19 are located near the distal and proximal ends 54, 55 of the cartridge and extend along a lateral direction (u). Hence, the side edge 17 is a distal side edge of the foil 11 whereas the oppositely-located side edge 19 is a proximal side edge of the foil 11.

The foil 11 and hence the entire sensor 10 is wrappable into a multi-wrapped or coiled configuration as shown in FIG. 7. In the present embodiment the foil is wrappable in an almost threefold manner. The foil 11 is wrappable to form a first or inner wrap 22, a second wrap 24 enclosing the first wrap 22 and further to form a third or outer wrap 26 substantially enclosing the second wrap. When in the wrapped configuration W the first wrap 22 has an inner diameter D that is equal to or slightly larger than an outer diameter of the tubular-shaped cartridge 50. In this way the cartridge 50 can be positioned and inserted into the first wrap 22 and hence inside the coiled or wrapped sensor 10.

The sensor 10, in particular its planar flexible foil 11 is divided into three zones, presently denoted as a sensing zone 12, a communication zone 14 and a protection zone 16. In lateral direction (u) the sensing zone 12 is confined by the later side edge 20 and in the opposite lateral direction by the communication zone 14. Further in lateral direction the communication zone 14 is located adjacent to the protection zone 16. The lateral edge 18 oppositely located to the lateral edge 20 forms a free end of the protection zone 16. All zones, hence the sensing zone 12, the communication zone 14 and the protection zone 16 extend over the entire longitudinal extension of the sensor 10. So the sensing zone 12, the communication zone 14 and the protection zone 16 all extend from the distal side edge 17 to the proximal side edge 19.

In the present embodiment the sensing zone 12 is provided with two measurement electrodes 32, 34 extending almost over the entire longitudinal extension (z) of the sensing zone 12. The lateral center regions of the measurement electrodes 32, 34 are typically located at a distance from each other that corresponds to half the circumference of the cartridge 50. So when in a final assembly configuration the two measurement electrodes 32, 34 are located on diametrically opposite sidewall sections of the cartridge 50.

In the present embodiment the substantially rectangularly-shaped electrodes 32, 34 are configured as capacity measurement electrodes. Hence, they are operable to measure an electric capacity therebetween. Since the electric susceptibility or permittivity of the piston 52 of the cartridge 50 clearly distinguishes from the electric susceptibility of the liquid substance 51 located therein, a measurement of the capacitance between the two electrodes 32, 34 is directly indicative of the axial or longitudinal position of the piston 52 inside the cartridge 50.

Apart from a substantially rectangular structure the electrodes 32, 34 may also comprise a tapered structure in axial direction. Moreover, the electrodes might be trapezoidal, triangular or may comprise a combination of a rectangular and a triangular shape. Especially by making use of electrodes having a geometric structure changing constantly in axial direction a respective linearly changing capacity signal is obtainable as for instance the piston 52 of the cartridge 50 is subject to a linear axial displacement in the course of a dispensing procedure. The geometric shape of the electrodes may hence improve the accuracy and precision of the capacity measurement. Moreover, it is conceivable that there are arranged multiple measurement electrodes along the longitudinal extension of the flexible foil 11, wherein pairs of measurement electrodes located at the same or at overlapping longitudinal positions are pair-wise connectable to a specific processor. By means of multiple pairs of first and second measurement electrodes, wherein said pairs are arranged at different longitudinal positions along the outer circumference of the cartridge's barrel a spatial resolution of an electric capacity measurement and hence a rather high spatial resolution of a position of a piston can be measured and determined by a processor connected to the various pairs of measurement electrodes.

When implemented as temperature measurement electrodes the electrodes may comprise pairs of heaters and thermistors that are pair-wise and alternately arranged in longitudinal direction along the cartridge's sidewall. Typically, the first measurement electrode may comprise several parallel oriented but longitudinally separated heaters whereas the second electrode comprises correspondingly arranged thermistors placed longitudinally between the heaters of the first measurement electrode. By means of the first electrode thermal energy can be deposited to the sidewall of the cartridge. By means of the various thermistors, hence by means of the second electrode temperature irregularities caused by the position of the piston inside the cartridge can be measured and determined. Typically, each branch of first and second electrodes forming a heater or a thermistor is separately connectable to a processor of the sensor assembly. In this way a thermal excitation and a heat transfer across the sidewall of the cartridge can be monitored with a spatial resolution in accordance to the distance of neighboring branches of first and second electrodes.

When configured and implemented as temperature measurement electrodes the measurement electrodes act as a thermal sensing array or like a thermal flow sensor.

Figure 4:
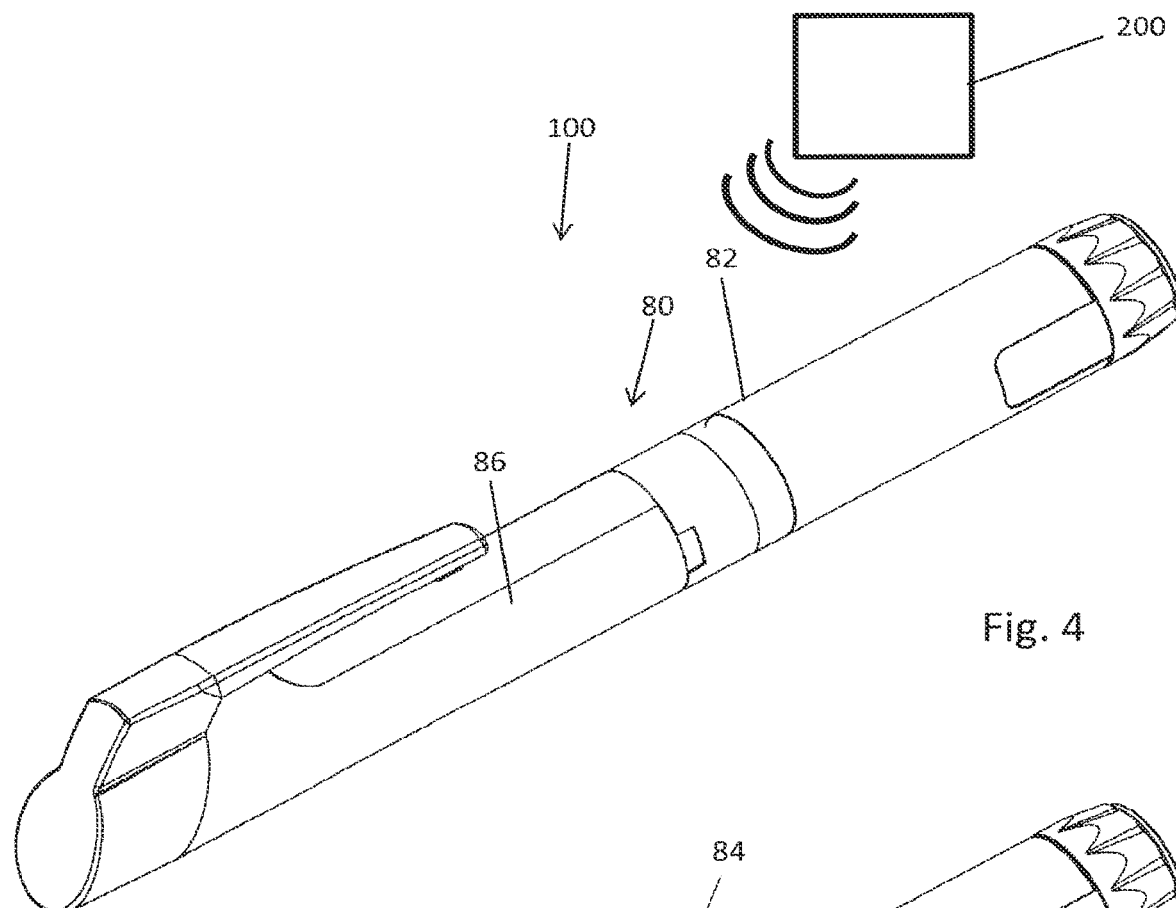
FIG. 4 shows a schematic perspective view of a pen-type injection device.
Figure 5:
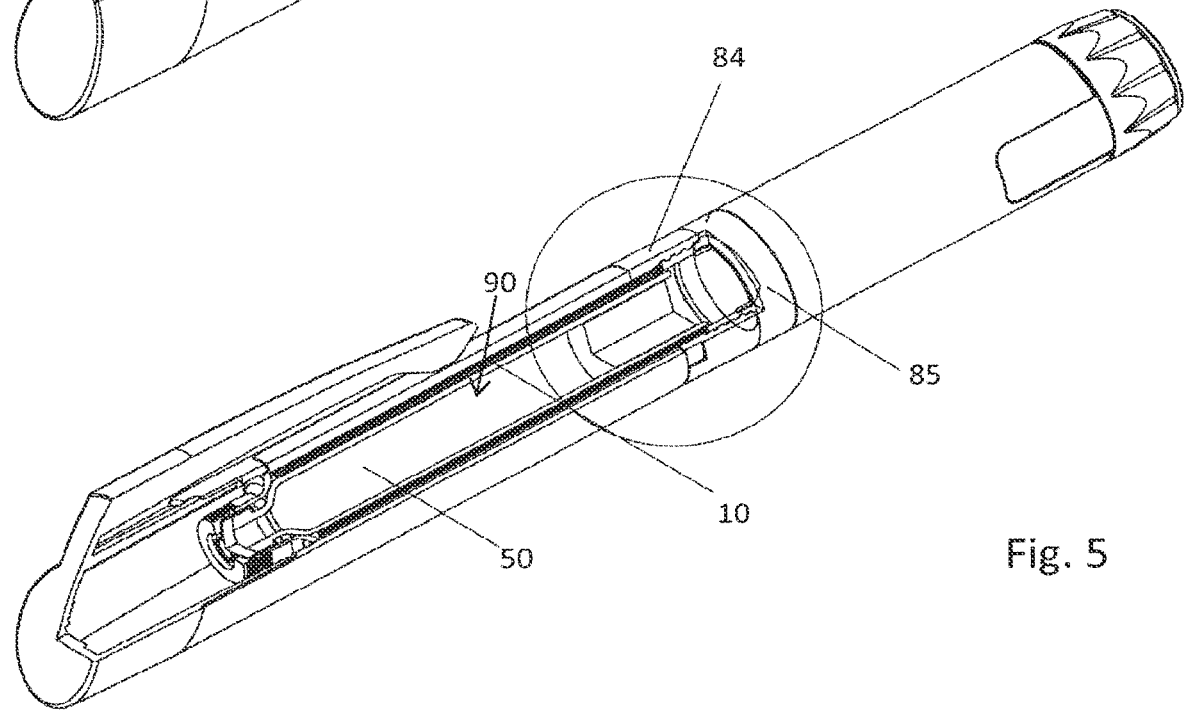
FIG. 5 shows the device according to FIG. 4 with a sidewall of its housing partially cut away.

The sensor 10 further comprises a processor 40 that is electrically connected with both electrodes 32, 34 via various conductors. The processor 40, typically implemented as a microcontroller is operable to trigger and to conduct a measurement by means of the electrodes 32, 34. The processor 40 is further configured to process measurement signals obtainable from the electrodes 32, 34. In addition, the sensor 10 is further equipped with an antenna 44 which is also electrically connected to the processor 40 via at least one conductor 42. By means of the antenna 44 the processor 40 is capable to communicate with external electronic devices 200 as schematically illustrated in FIG. 4. Typically, the antenna 44 provides a wireless communication between the processor 40 and the external electronic device 200. The antenna 44 may be designed as an RFID antenna or NFC antenna. The external electronic device 200 is then implemented as an RFID or NFC-capable device. The external electronic device 200 may be implemented as a smartphone, a smartwatch, a tablet computer or other electronic and data processing device capable to communicate with the processor 40 and hence with the sensor 10 in a wireless way.

The antenna 44 may not only provide wireless data transmission between the processor 40 and the external device 200 but is also operable to provide electrical energy to the processor 40 as well as to the electrodes 32, 34. Hence, the sensor 10 may be designed as a passive RFID or NFC label that does not require an own electrical energy supply.

The antenna 44 is typically located on a side 4 of the flexible foil 11 opposite to that side 3 of the foil 11 on which the electrodes 32, 34 are provided. While the electrodes 32, 34 are located on an inside-facing portion of the first wrap 22 the antenna 44 is located laterally offset in the communication zone 14 and hence on the outside-facing portion of the second wrap 24.

In addition the sensor 10 comprises an electrical shield 48 that is located on a side 3 opposite to that side 4 on which the antenna 44 is located. In this way the antenna 44 and the electrical shield 48 are electrically isolated or insulated by the non-conductive flexible foil 11.

The electrical shield 48 is also electrically connected to the processor 40. Signals obtainable from the electrical shield 48 may therefore be processed in order to discard an actual capacity measurement because the capacity actually measured by means of the electrodes 32, 34 may have been influenced by an external object, such like a finger of a person in the direct vicinity or in mechanical contact to the sensor 10.

Arrangement of all electrical components of the sensor 10 on a single and common foil 11 is of particular benefit since eventual electrical or mechanical interconnections between e.g. the electrodes 32, 34, the processor 40, the antenna 44 or the electrical shield 48 become superfluous. Moreover, it is intended that all electrically conducting structures of the sensor 10, namely the electrodes 32, 34, the conductors 42, the antenna 44 as well as the electrical shield 48 are attached to the flexible foil 11 by way of printing or by way of coating. The position and relative orientation of these electronic components or conductive structures is therefore fixed. It remains substantially unaffected during assembly of the sensor inside the drug delivery device 100. By making use of printed or coated conductive structures on the flexible foil 11 a large number of substantially identical sensors is producible 10 at low costs.

The electrical shield 48 may comprise at least two electrodes, each having a comb-like or meander-like structure, wherein such structures mutually mesh while being electrically separated. Hence, the electrical shield 48 serves to protect first and second electrodes 32, 34 against EMI emissions.

Typically and as it is apparent from a comparison of FIGS. 1 and 2 the electrical shield 48 and the antenna 44 are located on opposite sides 3, 4 of the flexible foil 11. In a wrapped configuration W the electrical shield 48 is located on an inside-facing portion of the second wrap 24 whereas the antenna 44 is located on an opposite outside-facing portion of the second wrap 24. In this way, the antenna 44 is located outside the electrical shield 48. In an implementation the processor 40 and the measurement electrodes 32, 34 are located on the same side 3 of the flexible foil 11. They may be also located on opposite sides of the foil 11. Then, an electric contact between the processor 40 and the electrodes 32, 34 may extend through the foil 11. The electric contact between the antenna 44 and the processor 40 extends through the foil 11. It is also conceivable, that the structure of the foil 11 is actually intersected by the processor 40 so that the processor 40 extends through the flexible foil 11. In this way and with regard to the coiled configuration W the processor 40 extends radially inwardly from the inner side 3 of the flexible foil 11 as well as radially outwardly from the outer side 4 of the flexible foil 11.

The flexible foil 11 further comprises at least a first section 13, 23 and a second section 15, 25. In the first section 13, 23 there is located at least one fastener 33, 36 attachable to the second section 15, 25 when the flexible foil 11 is in its wrapped configuration W. Hence, first and second sections 13, 23, 15, 25 are selected and defined such that they mutually or radially overlap when the flexible foil 11 is coiled up or wrapped. The fastener 33, 36 located in the first section 13, 23 is then capable to attach to the second section 15, 25. Typically, first and second mutually corresponding sections 13, 15 as well as 23, 25 are located in different but neighboring wraps 22, 24, 26 of the wrapped configuration W of the flexible foil 11.

By means of the at least one fastener 13, 23 at least any two of the wraps 22, 24, 26 or even all three wraps can be mutually fixed and mutually attached as the sensor 10 is in the wrapped configuration W. In this way an automatic de-coiling or unwrapping of the sensor 10 can be effectively prevented. This is of particular benefit for an assembly process of sensor and drug delivery device, in particular when the coiled or wrapped sensor 10 is to be inserted into a housing 80 of the drug delivery device 100 by a longitudinally-directed sliding motion.

In the presently illustrated embodiments various fastening techniques are illustrated. The first section 13 and the second section 15 as schematically illustrated in FIG. 1 are separated at a well-defined lateral distance d, which distance corresponds to the circumference of the second wrap 24. When in the wrapped configuration first and second sections 13, 15 then mutually overlap. The fastener 33 is presently provided by the processor 40 protruding from the plane of the foil 11. The second section 15 comprises a recess 35, which is presently configured as a depression in the flexible foil 11 or as a through opening in the flexible foil 11. The mutual lateral and longitudinal positions of the processor 40 and the recess 35 are selected such that the processor 40 substantially overlaps with the recess 35 when the flexible foil 11 is in the wrapped configuration W. Then the protruding processor 40 acting as the fastener 33 is insertable into the recess 33 and may even reach through the second section 15 of the flexible foil 11. In this way a positive interlock of at least two consecutive wraps 22, 24 or 26 of the flexible foil 11 can be obtained thereby preventing an automatic de-coiling or unwrapping.

Additionally or alternatively it is conceivable that the fastener 36 is located at the lateral edge 18 of the protection zone 16. In this embodiment the fastener 36 extends all over the longitudinal extension of the flexible foil 11. It may be provided with an adhesive on the inner side 3 of the flexible foil 11 so that when in the wrapped configuration the adhesive located in the first section 23 is attachable to a second section 25 located on the opposite, hence on the outer side 4 of the wrapped foil 11. Instead of an adhesive provided on or applied to the lateral edge 18 it is also conceivable, that at least the lateral edge itself 18 is bondable or weldable. Hence, said edge may be physically or chemically treated to provide a bonding or welding when, e.g. exposed to a bonding or welding agent or when exposed to thermal energy.

Using of an adhesive or of a bondable structure at the lateral side edge 18 to constitute the fastener 36 leads to a rather smooth tubular outer shape of the wrapped sensor 10. With the fastener 36 located at the lateral edge 18 the foil 11 can be coiled up into a wrapped configuration W without any radially outwardly protruding sections or portions. In such a configuration the wrapped sensor 10 is particularly suitable for insertion into a receptacle 90 of a housing 80 of a drug delivery device 100.

In FIGS. 4-6 and 8 an example of a drug delivery device 100 is presented. The drug delivery device 100 is configured as an injection device, in particular as a pen-type injection device. The drug delivery device 100 comprises a housing 80. The housing 80 comprises numerous housing components, namely a body 82 to accommodate and to house a drive mechanism 60. The housing 80 further comprises a cartridge holder 84 to receive the cartridge 50 and to receive and to accommodate the wrapped sensor 10. Furthermore, the housing 80 comprises a protective cap 86 detachably connectable to the cartridge holder 84 in order to protect at least the distal end thereof.

The drive mechanism 60 located in the body 82 forming a proximal end of the housing 80 comprises at least a piston rod or plunger to exert distally-directed pressure onto the piston 52 of the cartridge 50. In order to set and to dispense a dose of the medicament 51 the drive mechanism 60 comprises a dispensing button 62 and a dose dial 64. By way of the dose dial a dose of variable size can be selected and set by a user. By depressing the dispensing button 62 forming a proximal end face of the housing 80 a previously set dose of the medicament 51 can be dispensed, typically by way of injection.

The cartridge holder 84 comprises a tubular-shaped receptacle 90 confined by the sidewall of the cartridge holder 84. As it is apparent from FIG. 14a, the cartridge holder 84 comprises at least one window 88 in a sidewall that allows for a visual inspection of the cartridge 50 located therein. The distal end of the cartridge holder 84 is provided with a threaded socket in order to detachably connect a needle assembly, typically a needle hub to the cartridge holder. A double-tipped injection needle may then extend through a distal through opening of the cartridge holder in order to pierce a pierceable seal at the outlet end 54 of the cartridge 50.

Figure 6:
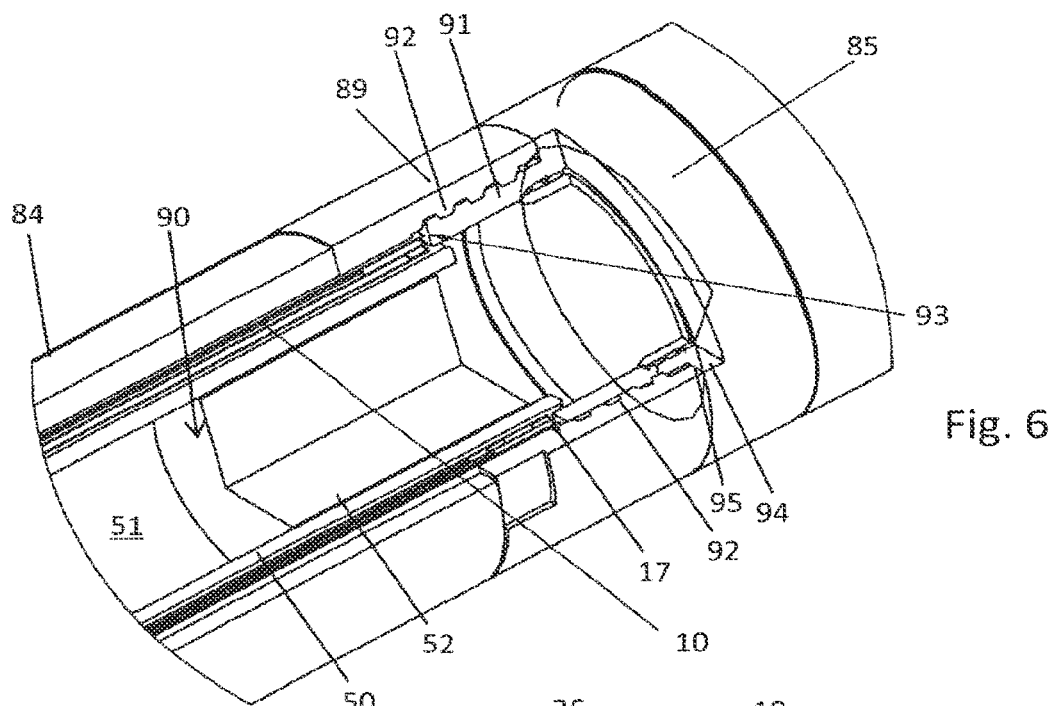
FIG. 6 shows a section of FIG. 5 in an enlarged view.

In the enlarged view according to FIG. 6 the wrapped sensor 10 is arranged inside the receptacle 90 of the cartridge holder 84. In FIG. 6, a proximal end of the cartridge holder, in particular the proximal interface to connect the cartridge holder 84 to the body 82 is shown in detail. The receptacle 90 of the cartridge holder 84 is delimited or confined in proximal direction by means of a detachable closure 85. The closure 85 as shown in FIG. 6 comprises a stepped down threaded section 91 extending in distal direction from the annular-shaped closure 85. The closure 85 comprises an outer diameter that is substantially identical to the outer diameter of the proximal end 89 of the sidewall of the cartridge holder 84.

The sidewall of the cartridge holder 84 at its proximal end 89 comprises a threaded section 92 that communicates and corresponds to the threaded section 91 of the closure 85. So by means of the mutually corresponding threaded sections 91, 92 the closure 85 can be detachably connected to the proximal end 89 of the cartridge holder 84. As it is apparent from FIG. 6 the threaded section 91 of the closure 85 comprises a well-defined radial thickness. In this way, a distal end of the threaded section 91 protrudes radially inwardly from the inside surface of the sidewall of the cartridge holder 84 as the closure 85 is fastened to the cartridge holder 84. In this way the distal end of the threaded section 91 forms a proximal stop 93 for the wrapped sensor 10. Hence, the coil proximal edge 19 of the wrapped sensor 10 may axially abut against the proximal stop 93 provided by the closure 85.

In proximal direction the threaded section 91 of the closure 85 is delimited or confined by a radially outwardly extending rim 94 having a radial extension that substantially corresponds to the thickness of the sidewall of the proximal end of the cartridge holder 84. In the assembly configuration as shown in FIG. 6 the rim 94 of the closure 85 axially abuts with a proximal end face 95 of the sidewall of the cartridge holder 84. In this way, a screw-type fastening of the closure 85 to the cartridge holder 84 can be delimited so as to prevent that the coiled sensor 10 located inside the cartridge holder's receptacle 90 is squeezed in longitudinal direction. The closure is generally of substantially annular shape so as to allow a longitudinal insertion if the cartridge therethrough. It is also conceivable that the cartridge 50 is axially fixed inside the cartridge holder 84 by means of the closure. Then the through opening of the closure can be as small as to allow the piston rod to pass through.

At its proximal end the closure 85 may comprise a central through opening to receive a fastening structure of the body 82. For instance, the proximal end of the closure 85 may be provided with an inner thread to threadedly engage with a correspondingly-shaped threaded section 81 of the body as indicated in FIG. 14a. Instead of a threaded connection of cartridge holder 84 and closure 85 other fastening mechanisms, such like a clip-based fastening mechanism of cartridge holder 84 and closure 85 is also conceivable. Moreover, also the connection between body 82 and cartridge holder 84 or between body 82 and closure 85 may be configured as a threaded connection or in form of a different type of connection, that is e.g. of positive locking type, such like a clip-based interconnection.

In FIGS. 9-11 the wrapping or coiling of the sensor 10 is illustrated in three consecutive steps. For coiling or wrapping the sensor 10 to form a coiled tubular structure as shown in FIGS. 7 and 11 the sensor 10 is coiled on a tubular-shaped rod 110 of a coil-forming tool 112. For this the lateral edge 20 of the flexible foil 11 is initially attached to the outer circumference of the tubular-shaped rod 110.

Thereafter, the sensor 10 is coiled or wrapped around the outer circumference of the rod 110, thereby forming the first wrap 22, the second wrap 24 and the third wrap 26. Finally, as the opposite lateral edge 18 of the flexible foil 11 is subject to a coiling or wrapping the adhesive located along the lateral edge 18 serves to attach to the second section 25 located on the outer side 4 of the flexible foil 11. By way of the adhesive of the fastener 36 in the first section 23 the lateral edge 18 can be permanently fastened to the outside-facing side of the second wrap 24. Thereafter the so-formed tubular-shaped coiled or wrapped sensor 10 can be withdrawn from the tubular-shaped rod 110. It is then insertable into the receptacle 90 from a proximal end 89 of the cartridge holder 84 towards the distal direction 1 as it is apparent from a comparison of FIGS. 14*a* and 14*b*.

In order to facilitate fastening of the lateral edge 20 to the coil-forming rod 110 the lateral edge may be provided with a fixing section 38. The fixing section 38 located on the inner side 3 of the wrappable flexible foil 11 may be provided with an adhesive that is detachable from the rod 110. In this way and by means of the fixing section 38 at the lateral side edge 20 of the flexible foil 11 the flexible foil 11 can be temporally and detachably fixed to the coil-forming rod 110 at least for the duration for forming the wrapped sensor 10.

Thereafter and as it is apparent from a comparison of FIGS. 14*b* and 14*c* the closure 85 is connected to the proximal end 89 of the cartridge holder 84, thereby fastening and fixing the coiled sensor 10 inside the cartridge holder 84. In a further step of assembly as it is apparent from a comparison of FIGS. 14*c* and 14*d*, the cartridge 50 is actually inserted in longitudinal direction through the closure 85 and into the receptacle 90 of the cartridge holder 84. In a final steps of assembly as apparent from a comparison of FIGS. 14*d* and 14*e* the proximal end 89 of the cartridge holder 84, hence a proximal end of the closure 85 is connected with a distal end of the body 82 of the housing 80 of the drug delivery device 100. Finally, the protective cap 86 is to be attached to the cartridge holder 84 or to the body 82 in order to enclose the cartridge holder 84 and to protect the cartridge 50 located therein.

Figure 12:
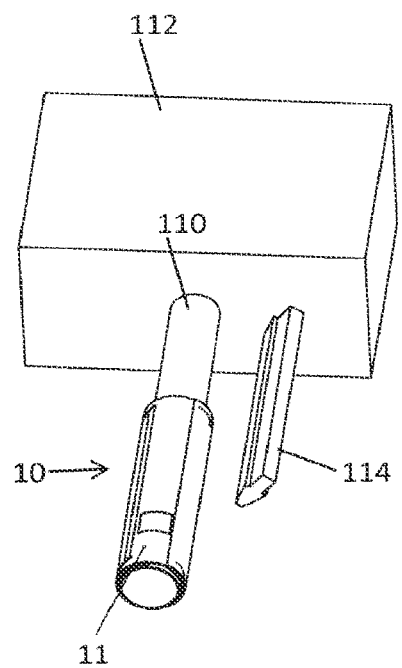
FIG. 12 shows an intermediate step of coiling the sensor according to a further embodiment.
Figure 13:
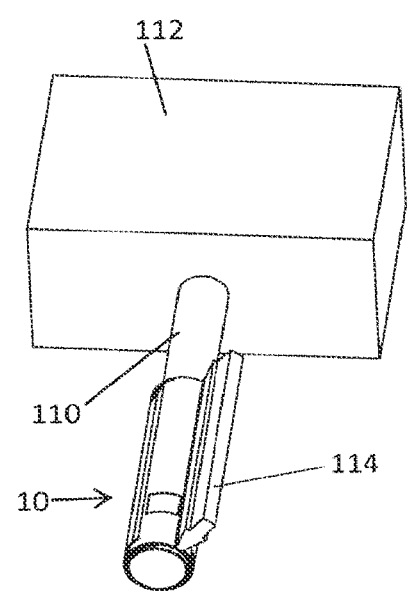
FIG. 13 shows the sensor during a welding-based fastening of fastener and second section.

In FIGS. 12 and 13 a different way of fastening the fastener 36 to the second section 25 is illustrated. There, the fastener 36 comprises a bondable or weldable structure. By means of a correspondingly-shaped welding or bonding tool 114 as shown in FIGS. 12 and 13 the lateral edge 18 can be permanently attached or welded to the second section 25 of the flexible foil 11 located radially underneath. It is particularly conceivable, that the welding tool 114 is configured to apply heat to the fastener 36 so as to form a persistent and long-lasting bonding of the lateral edge 18 to the second wrap 24.

The adhesive, bonded or welded attachment of the first section 23 to the second section 25 is conceivable as an alternative or in addition to the positive interlock obtainable by the processor 40 protruding from the plane of the flexible foil 11 and intersecting or engaging the recess 35 in the flexible foil 11.

LIST OF REFERENCE NUMBERS

1 distal direction
2 proximal direction
3 inner side
4 outer side
10 sensor
11 flexible foil
12 sensing zone
13 first section
14 communication zone
15 second section
16 protection zone
17 edge
18 edge
19 edge
20 edge
22 first wrap
23 first section
24 second wrap
25 second section
26 third wrap
32 measurement electrode
34 measurement electrode
33 fastener
35 recess
36 fastener
38 fixing section
40 processor
42 conductor
44 antenna
48 electrical shield
50 cartridge
51 medicament
52 piston
54 outlet end
55 proximal end
60 drive mechanism
62 dispensing button
64 dose dial
80 housing
81 threaded section
82 body
84 cartridge holder
85 closure
86 cap
88 window
89 proximal end
90 receptacle
91 threaded section
92 threaded section
93 proximal stop
94 rim
95 end face
100 drug delivery device
110 rod
112 tool
114 welding tool

The invention claimed is:

1. A sensor for measuring at least one physical or chemical parameter of a cartridge filled with a liquid substance, the sensor comprising:
  a planar flexible foil having a sensing zone and a communication zone adjacently arranged in a lateral direction;
  the planar flexible foil further comprising a first section and a second section, the second section being separated from the first section, the first section being located between and extending along the sensing zone and the communication zone;
  at least one measurement electrode located in the sensing zone on the flexible foil, the communication zone being void of measurement electrodes; and
  at least one fastener located in the first section and configured to attach to the second section for keeping the flexible foil in a wrapped configuration, wherein the flexible foil is configured to be wrapped into the wrapped configuration in which the sensing zone of the flexible foil forms at least a first inner wrap with an inner diameter that is equal to or larger than an outer diameter of the cartridge, and wherein in the wrapped configuration, the first section is at least partially in direct contact with the second section.

2. The sensor according to claim 1, wherein when the flexible foil is in the wrapped configuration the first section and the second section are at least partially in direct surface contact.

3. The sensor according to claim 1, wherein the at least one fastener is positioned at a lateral side edge of the flexible foil.

4. The sensor according to claim 1, wherein the at least one fastener located in the first section comprises an adhesive and is configured to be adhesively attached to the second section of the flexible foil when the flexible foil is in the wrapped configuration.

5. The sensor according to claim 1, wherein the at least one fastener located in the first section comprises a structure configured to be bonded or welded to the second section of the flexible foil when the flexible foil is in the wrapped configuration.

6. The sensor according to claim 1, wherein the at least one fastener and the second section are located on opposite sides of the flexible foil.

7. The sensor according to claim 1, wherein the at least one fastener located in the first section protrudes from a plane of the flexible foil and wherein the second section comprises a recess configured to receive the at least one fastener when the flexible foil is in the wrapped configuration.

8. The sensor according to claim 7, wherein the protruding at least one fastener fits into the recess when the flexible foil is in the wrapped configuration and wherein the protruding at least one fastener and the recess form a positive interlock operable to prevent unwrapping or de-coiling of the wrapped flexible foil.

9. The sensor according to claim 1, further comprising a processor electrically connected to the at least one measurement electrode.

10. The sensor according to claim 9, wherein at least a portion of the processor protrudes from a plane of the flexible foil and forms the at least one fastener configured to be received by a recess of the second section.

11. The sensor according to claim 9, further comprising an antenna located in the communication zone of the flexible foil, the antenna being electrically connected to the processor.

12. The sensor according to claim 9, further comprising an electrical shield located on the flexible foil, the electrical shield being electrically connected to the processor.

13. The sensor according to claim 11, further comprising an electrical shield located in the communication zone of the flexible foil on a side of the flexible foil opposite to another side of the flexible foil on which the antenna is located.

14. The sensor according to claim 11, wherein the sensing zone and the communication zone of the flexible foil are adjacently arranged in the lateral direction such that the sensing zone forms the first wrap and the communication zone forms a second wrap enclosing the first wrap when the flexible foil is in the wrapped configuration.

15. The sensor according to claim 14, wherein the flexible foil further comprises a protection zone adjacently located to the communication zone and being configured to form a third wrap enclosing the second wrap when the flexible foil is in the wrapped configuration.

16. A drug delivery device for setting and dispensing of a dose of a liquid medicament, the drug delivery device comprising:
a housing comprising:
a tubular shaped receptacle configured to accommodate a cartridge filled with the liquid medicament; and
a sensor arranged and fixed inside the tubular shaped receptacle in a wrapped configuration to receive the cartridge inside a first wrap, the sensor comprising:
a planar flexible foil having a sensing zone and a communication zone adjacently arranged in a lateral direction;
the planar flexible foil further comprising a first section and a second section, the second section being separated from the first section, the first section being located between and extending along the sensing zone and the communication zone;
at least one measurement electrode located in the sensing zone on the flexible foil, the communication zone being void of measurement electrodes; and
at least one fastener located in the first section and configured to attach to the second section for keeping the flexible foil in the wrapped configuration,
wherein the flexible foil is configured to be wrapped into the wrapped configuration in which the sensing zone of the flexible foil forms at least the first inner wrap with an inner diameter that is equal to or larger than an outer diameter of the cartridge, and wherein in the wrapped configuration, the first section is at least partially in direct contact with the second section.

17. The drug delivery device according to claim 16, wherein the tubular shaped receptacle is located in a cartridge holder of the housing, wherein a proximal end section of the cartridge holder accommodating the cartridge is configured to be detachably connected with a distal end section of a body of the housing, and wherein the body of the housing accommodates a drive mechanism configured to exert distally directed pressure on a piston of the cartridge.

18. The drug delivery device according to claim 16, wherein the at least one fastener located in the first section comprises an adhesive and is configured to be adhesively attached to the second section of the flexible foil when the flexible foil is in the wrapped configuration.

19. The drug delivery device according to claim 16, wherein the sensor further comprises a processor electrically connected to the at least one measurement electrode, wherein the at least one measuring electrode is located in a sensing zone of the flexible foil.

20. A sensor for measuring at least one physical or chemical parameter of a cartridge filled with a liquid substance, the sensor comprising:
a planar flexible foil having a first section and a second section, the second section being separated from the first section;
at least one measurement electrode located on the flexible foil;
at least one fastener located in the first section and configured to attach to the second section for keeping the flexible foil in a wrapped configuration,
wherein the flexible foil is configured to be wrapped into the wrapped configuration in which the flexible foil forms at least a first wrap with an inner diameter that is equal to or larger than an outer diameter of the cartridge, and wherein in the wrapped configuration, the first section is at least partially in direct contact with the second section; and
a processor electrically connected to the at least one measurement electrode,
wherein at least a portion of the processor protrudes from a plane of the flexible foil and forms the at least one fastener configured to be received by a recess of the second section.

* * * * *